United States Patent [19]
Levine et al.

[11] Patent Number: 4,804,518
[45] Date of Patent: Feb. 14, 1989

[54] DEVICE FOR OCCULT BLOOD TESTING

[76] Inventors: Robert A. Levine, 31 Pilgrim La., Guilford, Conn. 06437; Stephen C. Wardlaw, 128 Sunset Hill Dr., Branford, Conn. 06405

[21] Appl. No.: 704,962

[22] Filed: Feb. 25, 1985

[51] Int. Cl.⁴ .................... G01N 21/78; G01N 33/72
[52] U.S. Cl. ........................ 422/56; 422/58; 422/61; 435/28; 435/805; 436/66
[58] Field of Search ............ 436/66, 169, 170; 422/56, 57, 58, 61; 128/638, 749, 756, 759; 435/28, 805

[56] References Cited

U.S. PATENT DOCUMENTS

| 3,996,006 | 12/1976 | Pagano | 422/50 |
|---|---|---|---|
| 4,175,923 | 11/1979 | Friend | 422/56 K |
| 4,225,557 | 9/1980 | Hartl et al. | 422/56 |
| 4,259,964 | 4/1981 | Levine | 422/61 K |
| 4,273,741 | 6/1981 | Levine | 422/58 X |
| 4,328,184 | 5/1982 | Kondo | 422/58 |
| 4,365,970 | 12/1982 | Lawrence et al. | 436/66 |
| 4,367,750 | 1/1983 | Levine | 128/638 |
| 4,420,353 | 12/1983 | Levine | 156/227 |
| 4,486,536 | 12/1984 | Baker et al. | 422/58 X |
| 4,541,987 | 9/1985 | Guadagno | 422/56 |
| 4,559,949 | 12/1985 | Levine | 128/638 |

FOREIGN PATENT DOCUMENTS 0124214 11/1984 European Pat. Off. .
0124215 11/1984 European Pat. Off. .
2031583 4/1980 United Kingdom .

Primary Examiner—Barry S. Richman
Assistant Examiner—Robert J. Hill, Jr.
Attorney, Agent, or Firm—Price, Heneveld, Cooper, DeWitt & Litton

[57] ABSTRACT

The device consists of a base sheet of impermeable plastic such as vinyl, or the like, and a guaiac stool receptor sheet adhesively secured thereto. The base sheet is sufficiently larger than the receptor sheet so to form an impermeable skirt which surrounds the receptor sheet so as to form an hermetic barrier protecting the receptor sheet on the underneath one of two of the devices when stacked one on top of the other. A performance/control monitor is included on the device. The monitor includes a peroxidatively active material such as hematin, or the like, which confirms the reactively of the guaiac-impregnated sheet, as well as the activity of the peroxide developing solution. The monitor material is kept out of reactive contact with the guaiac receptor sheet until the developer reagent is applied to the device. A stack of the devices is packed in a sealed container of plastic, or the like, so that the individual devices can be removed from the container one at a time. The devices are designed for use in the physician's office for reception of stool smears taken manually on a rubber glove or finger cot by the physician from patients.

7 Claims, 4 Drawing Sheets

DEVICE FOR OCCULT BLOOD TESTING

This invention relates to a device for use in testing stool for occult blood. More particularly, this invention relates to such a device which is inexpensive to produce, which is designed for use by physicians in their offices, and which includes a performance/control monitor.

Many devices have been suggested in the prior art for use in obtaining stool samples for analysis for occult blood. Typical of such devices are those disclosed in U.S. Pat. Nos. 3,996,006 to Pagano; 4,175,923 to Friend; 4,365,970 to Lawrence; 4,259,964 to Levine; and 4,273,741 to Levine.

The above-listed patents all disclose stool sampling devices which are designed for use by a patient, generally in the privacy of the home. At present, when stool samples are taken in the physician's office by the doctor with the use of a rubber glove during a rectal examination, the stool is smeared on a sheet of guaiac-impregnated paper and a developer reagent is applied to the stool smear to ascertain the presence or absence of occult blood in the stool. The guaiac-impregnated sheets presently used in the physician's office do not include any performance/control monitor which will indicate the reactive state of the guaiac when the developer reagent is applied to it. The guaiac reagent used in occult blood testing of stool is susceptible to degradation when exposed to air and/or to light. The guaiac-impregnated sheets presently used by physicians in their offices are permeable to air and are not packaged to ensure shielding from light or air circulation. Thus, a stack of such sheets, even when disposed in a carton, is subject to exposure to light and/or air and, thus, prone to degradation of the guaiac during storage of the sheets. It is apparent that a stool sample analyzed on a sheet of degraded guaiac paper, which does not have a performance/control monitor associated therewith, can give an invalid reading in that no color change will appear even though the stool has blood in it.

The device of this invention is designed for use in the physician's office and serves as a receptor of a stool smear applied to it from the physician's rubber glove. The sample is taken from the patient by the physician inserting the finger of a rubber glove clad hand into the patient's rectum. The testing device includes an impermeable base sheet of pliant plastic material such as vinyl, or the like. Disposed on the impermeable sheet is an absorbant stool receptor sheet of guaiac-impregnated paper, or the like. The receptor sheet is sufficiently smaller than the base sheet so that a skirt surrounding the receptor sheet is formed by the margins of the base sheet. This skirt is impermeable to air and moisture. Disposed on the device, as for example on one corner of the receptor sheet, is a performance/control monitor formed from hematin or some other peroxidatively active reagent which causes a change in color when the developer reagent is applied to the monitor and the guaiac sheet. The performance/control monitor verifies the condition of the guaiac, as well as the developing solution. The monitor reagent is kept out of reactive relationship with the guaiac-impregnated sheet until the developer reagent is added. This prevents formation of a heme-guaiac complex which can form in the prior art devices when the peroxidase positive reagent is applied directly to the guaiac sheet. Such heme-guaiac complexes as exist in the prior art can give a false indication of a properly functioning test system, due to the fact that the heme-guaiac complex is more resistant to light and air degradation than the plain guaiac paper.

The devices may be packaged in stacks of about one hundred, and each stack is disposed in an air-tight opaque container which is preferably made from a relatively rigid plastic material, such as polystyrene or ABS. Inside the container is a spring loaded follower which pushes the stack toward one end of the container. A slot is formed in the side of the container near that one end, the slot providing a port for withdrawing the devices one at a time from the container. The container can be secured to a mount which is fastened to a wall in the physician's laboratory, or, can be provided with suction mounts capable of securing the container to a lab bench. The end of the container housing the spring is recessed to provide a well for containment of a bottle of the developer reagent. The well also serves as a spring guide for the follower spring.

It is, therefore, an object of this invention to provide a device suitable for use in a physician's office by the physician for analyzing stool samples for the presence or absence of occult blood.

It is a further object of this invention to provide a device of the character described which includes a performance/control monitor to verify the validity of the test results observed.

It is an additional object of this invention to provide a device of the character described wherein the performance/control monitor includes a peroxidatively active reagent which is kept out of reactive contact with the guaiac-impregnated sheet until the developer reagent is applied to the device.

It is another object of this invention to provide a device of the character described which is adapted to be packaged in an air-tight, yet loose, stack to protect the guaiac reagent against degradation during storage.

It is yet another object of this invention to provide a device of the character described wherein the devices are dispensed from a stack thereof disposed in an opaque container which protects the guaiac reagent from exposure to light.

BRIEF DESCRIPTION OF THE DRAWINGS

These and other objects and advantages of the invention will become more readily apparent from the following detailed description of preferred embodiments of a device formed in accordance with the invention when taken in conjunction with the accompanying drawings, in which:

Referring now to the drawings, there is shown in FIGS. 1 and 2 a preferred embodiment of a stool testing device denoted generally by the numeral 2, which is formed in accordance with this invention. The device 2 includes a basal sheet 4 which is formed from a plastic such as vinyl, or a plastic-paper laminate, or some other pliant material which is impermeable to moisture and air. A guaiac-impregnated stool receptor sheet 6 is adhesively secured to the basal sheet 4 and a performance/control monitor 8 is secured to the receptor sheet 6. The receptor sheet 6 is preferably a fibrous paper member, and the monitor 8 includes a base part 10 made from paper or some similar material, and a button part 12 which is deposited on the base part 10 and which contains the absorbed hematin reactant. The base part 10 of the monitor 8 serves to chemically isolate the hematin reactant from the guaiac in the receptor sheet 6. Thus, the base part 10 of the monitor 8 prevents the hematin reactant from combining with the guaiac to form a heme-guaiac complex which, as previously noted, could provide a false indication that the guaiac in the receptor sheet is still viable when the developer reagent is applied to the monitor 8. When the developer reagent, such as peroxide, is applied to the button 12, the hematin is eluted from the button and the developer and hematin solution spill over the edges of the base part 10 onto the guaiac-impregnated receptor sheet 6. If the guaiac is still viable, the characteristic blue color will appear about the base part 10. FIG. 3 illustrates the manner in which the receptor sheet 6 is secured to the basal sheet 4 by adhesive areas A and, also, illustrates the manner in which the reagent button 12 is deposited on the base 10 of the performance/control monitor 8.

Figure 2:
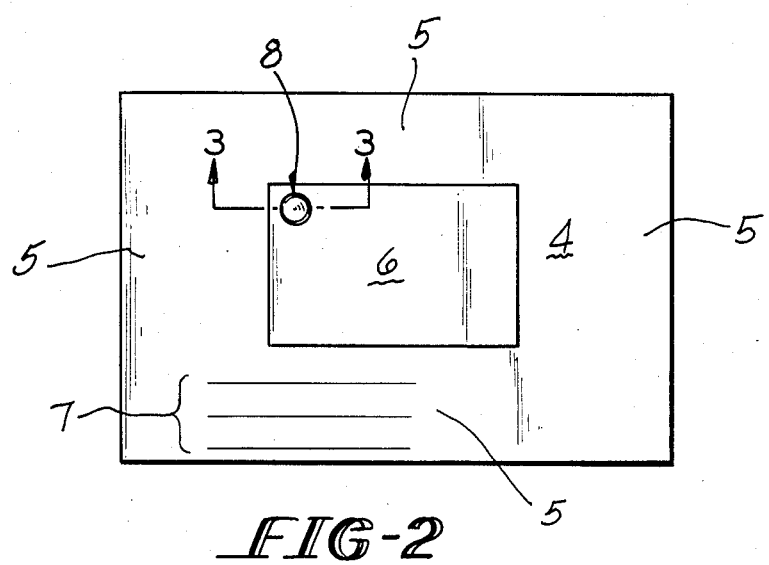
FIG. 2 is a top plan view of the device of FIG. 1.
Figure 3:
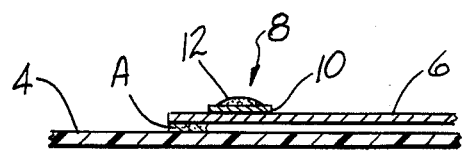
FIG. 3 is a fragmented sectional view taken along line 3—3 of FIG. 2.

It will be noted from FIG. 2 that the basal sheet 4 extends outwardly beyond the edges of the receptor sheet 6 sufficiently to form a protective skirt 5 surrounding the receptor sheet 6. A patient identification area 7 can be provided on the skirt 5, if so desired.

The device is used as follows. Once the stool sample is obtained by the physician, a smear is wiped off the rubber glove onto the receptor sheet 6 approximately in the center thereof. The developer reagent is then applied to the stool smear on the receptor sheet and, also, to the performance/control monitor 8. If the characteristic blue color is observed about the stool smear and the monitor, then the presence of occult blood in the stool is confirmed. If the blue color appears only at the monitor 8, then the absence of occult blood in the stool is confirmed. If no blue color appears at the monitor location, then the degradation of the quaiac and/or the developing solution is confirmed, and a second test is made with new reagents.

Figure 4:
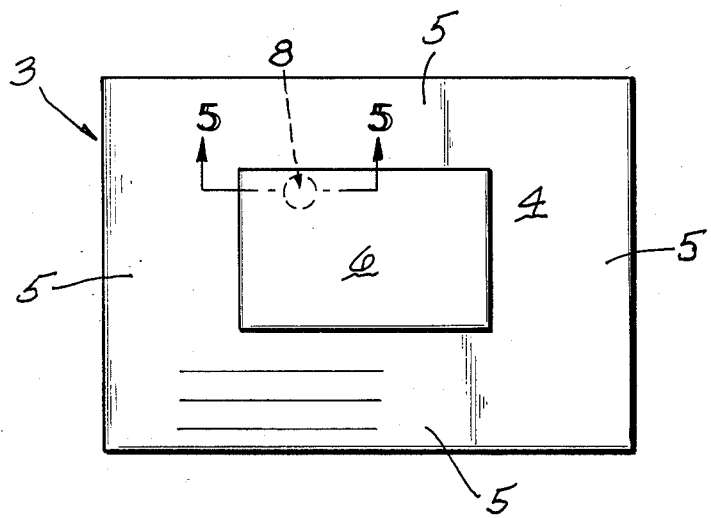
FIG. 4 is a top plan view similar to FIG. 2 but showing a second embodiment of the device of this invention.
Figure 5:
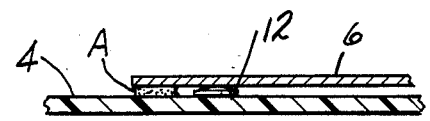
FIG. 5 is a fragmented sectional view taken along 5—5 of FIG. 4.

Referring now to FIGS. 4 and 5, a second embodiment of the device is shown. The second embodiment 3 includes a basal sheet 4 of pliant impermeable material, having adhered thereto a smaller stool receptor sheet 6. The basal sheet 4 is sufficiently larger than the receptor sheet 6 so as to form an impermeable protective skirt 5 surrounding the receptor sheet 6. The performance/-control monitor 8 is disposed on the basal sheet 4 beneath a marginal portion of the receptor sheet 6. The receptor sheet 6 is secured to the basal sheet 4 by adhesive areas A, and the monitor 8 includes the peroxidatively active reagent button 12 which can be deposited directly on the basal sheet 4, or can be on a base member as previously described, which base member is, in turn, secured to the basal sheet 4. The receptor sheet 6 is dry, and the reagent button 12 is also dry prior to application of the stool sample and developer reagent. Since both of these elements are dry, the peroxidase positive reagent will not be in chemically reactive contact with the quaiac until the developer solution wets both the receptor sheet 6 and the reagent button 12 and causes all of the chemicals to reactively intermingle. Thus, the device, while including a performance/control monitor, will not produce a heme-quaiac complex during storage prior to use.

The device is used in the same manner as previously described with the exception that the developer reagent is applied to the receptor sheet 6 over the monitor button 12, whereupon the color change leaches through the receptor sheet 6.

Figure 1:
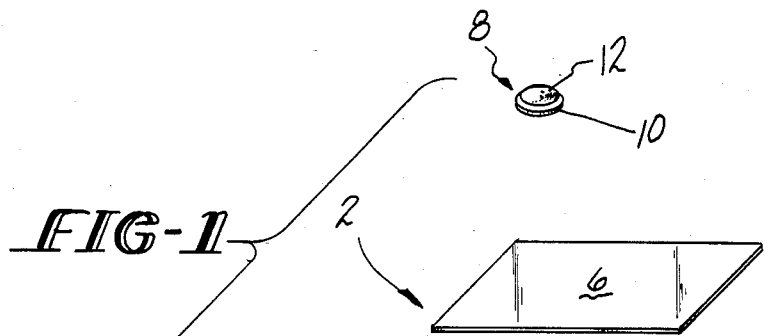
FIG. 1 is an exploded perspective view of a first embodiment of a device formed in accordance with this invention.
Figure 6:
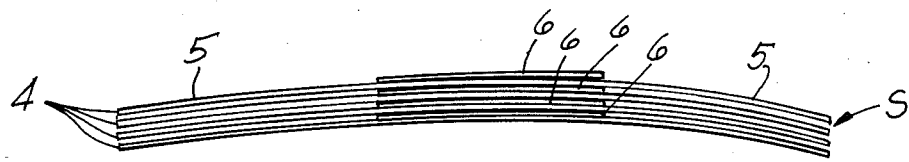
FIG. 6 is a side elevational view of a stack of the devices shown in FIG. 2 or 4.
Figure 9:
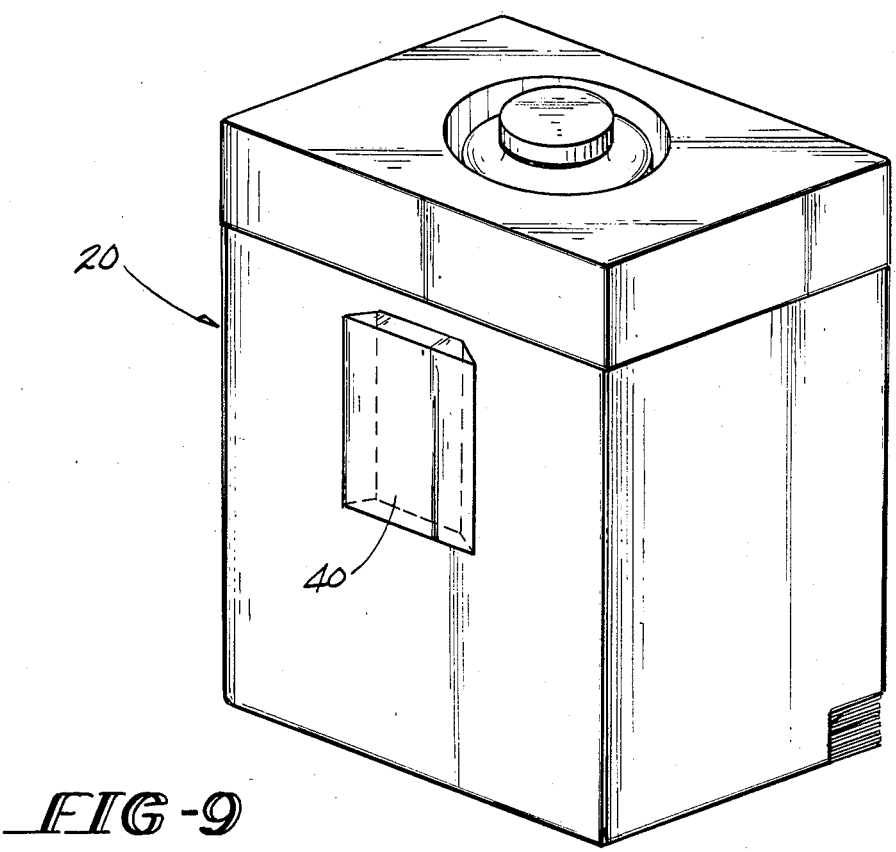
FIG. 9 is a perspective view similar to FIG. 7 but showing the back of the container.

Referring now to FIG. 6, a stack of the devices of FIG. 1 or 4 is shown. The stack S is formed so that the devices therein are aligned so as to provide relatively uniform margins for the stack. Thus, the receptor sheets 6 are disposed generally in vertical alignment, and the skirt portions 5 of the basal sheets 4 overlie each other to form the margins of the stack S. It will be appreciated that the skirt portions of the individual devices overlie each other closely so that when two of the devices are disposed atop each other, the impermeable basal sheets envelope the receptor sheet on the lowermost of the two devices to protect it from air, moisture and light. Thus, in a stack of the devices, each receptor sheet except the uppermost one is protected so as to guard against degradation of the guaiac. The skirt portions 5 of each basal sheet 4 must be extensive enough to thusly protect the receptor sheet 6 on the underlying device.

Figure 10:
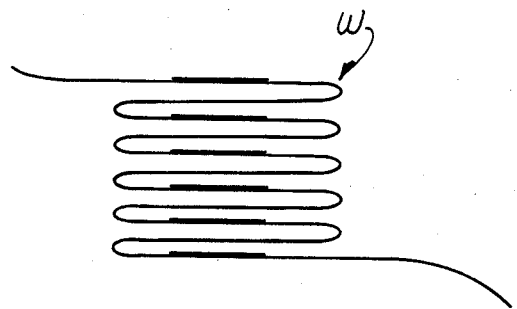
FIG. 10 is a side elevational view of a stack of devices made in accordance with this invention which are formed as part of a continuous strip.
Figure 11:
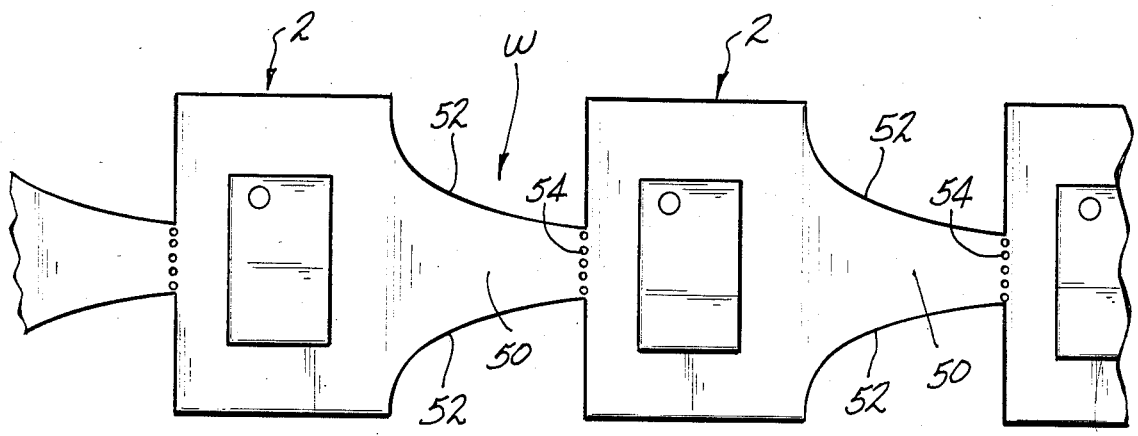
FIG. 11 is a plan view of the strip of FIG. 10.

Referring to FIGS. 10 and 11, an alternative form of the device of this invention is shown which is produced in strip form. The strip has a continuous web W formed from the impermeable plastic material. The devices 2 are serially arranged on the strip, with adjacent devices 2 being interconnected by flaps 50. Each flap 50 is integral with an associated one of the devices 2 and has edges 52 which converge toward a tear line 54 connecting the flaps 50 with the next adjacent device. The web W is folded as shown in FIG. 10 and, thus, packaged in a container as previously described. To dispense the devices, one pulls the lead flap 50, its attached device 2, and the next flap 50 out of the container. One then ruptures the tear line 54 leaving the trailing flap projecting from the container for easy grasping when the next device is to be dispensed.

Figure 7:
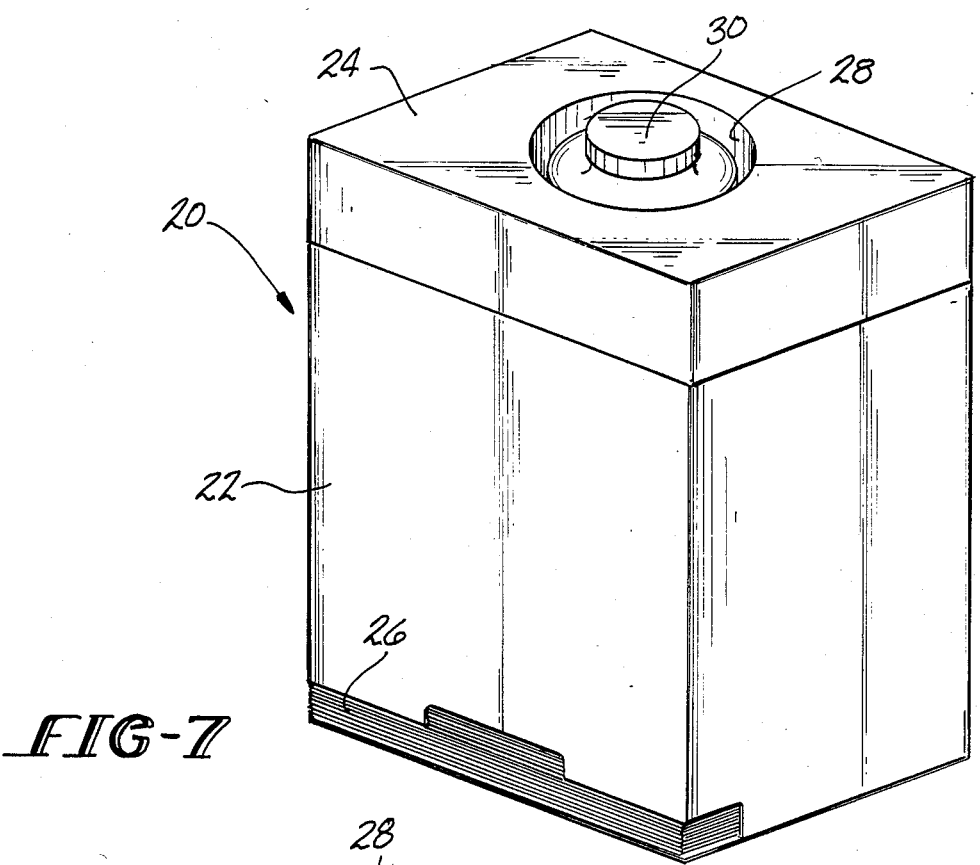
FIG. 7 is a perspective view of a container adapted for holding a stack of the devices of this invention for dispensing individual ones of the devices from the stack.

Referring now to FIG. 7, there is shown a preferred embodiment of a container from which the devices can be individually dispensed in the physician's office. The container, denoted generally by the numeral 20, includes a bottom part 22, and a top part 24 which is snap fitted onto the bottom part 22. The two parts are preferably made from injection molded plastic, such as polystyrene or ABS. The container 20 has approximately the same cross sectional area as the stack of devices previously shown so that the stack retains its configuration when placed in the container. A dispensing slot 26 is formed at a bottom corner of the container to allow individual devices to be drawn from the bottom of the stack and out of the container. The slot 26 will initially be closed by a strip of impermeable tape, or the like. The top part 24 of the container 20 is formed with a well 28 in its upper surface for the reception and storage of a bottle 30 of the developing reagent.

Figure 8:
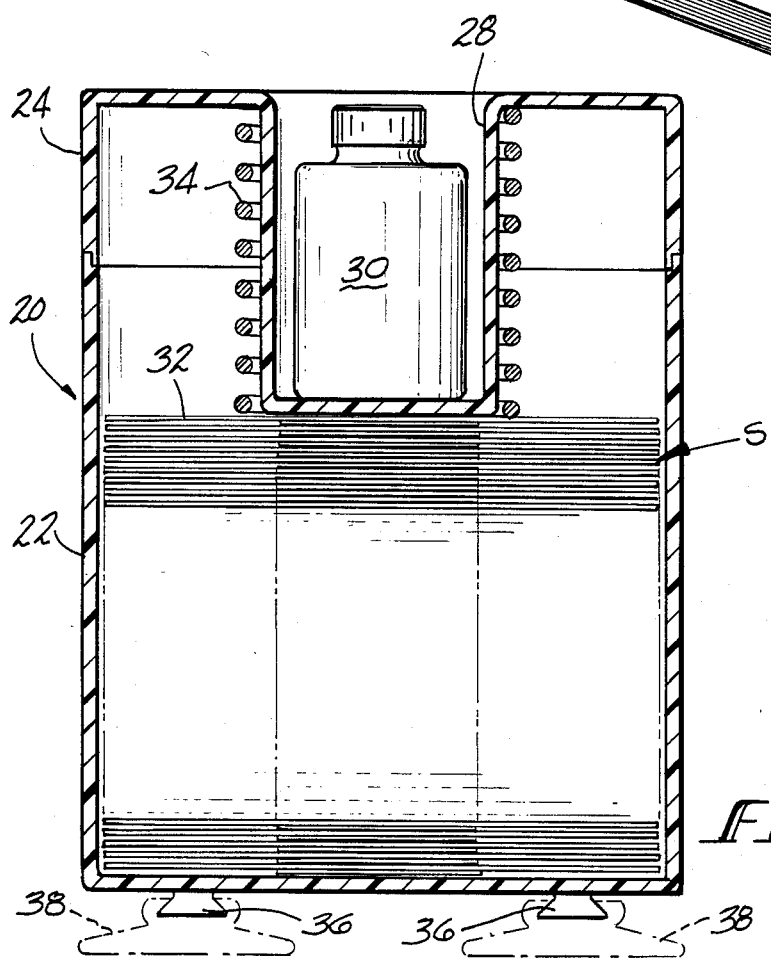
FIG. 8 is a sectional view of the container of FIG. 7 showing the manner in which the devices are held therein.

Referring to FIG. 8, the interior of the container 20 is shown. The stack S of devices is biased downwardly in the container 20 by a follower 32 which, in turn, is biased by a follower spring 34. The spring 34 is a coil spring which ensleeves the well 28 so that the wall of the well 28 serves as a spring guide for the follower spring 34. The follower 32 will preferably be formed from an impermeable material so as to protect the receptor sheet on the topmost device in the stack S. It will be noted that the developer reagent bottle 30 preferably fits completely within the well 28 so that the entire package can be shrink-wrapped for shipment to physicians' offices. The bottom of the container 20 may be provided with profiled projections 36 integral with the remainder of the container which are adapted to have rubber suction cups 38 (shown in phantom) secured thereto. The suction cups 38 adapt the container for securement to the top of a lab bench, or the like.

Alternatively, the back wall of the container 20 may be formed with an integral rib 40 which is profiled so as to be removably slidably insertable into a mating slot formed in a mounting piece which can be fastened to a wall in the physician's office.

It will be readily appreciated that the device of this invention is inexpensive to produce and yet dependable in operation. The provision of a performance/control monitor on the device which is not in a chemically reactive relationship with the receptor sheet until the developer reagent is added to the device ensures proper operation of the monitor. The developer reagent wets the peroxidatively active monitor reagent and the guaiac and allows both to combine in the chemical reaction which results in the characteristic color change when the guaiac has not degraded during storage. The devices are formed so that the guaiac impregnated receptor sheets will be protected against air, moisture, and light when the devices are disposed in a stack. The stacks are packaged in opaque containers which have means for spring loading the stack so that individual ones of the devices can be drawn from the container from the bottom of the stack. The container has a well in its top wall which serves as a spring guide for the spring loading means and also houses a bottle of developer reactant used in the testing.

Since many changes and variations of the disclosed embodiments of the invention may be made without departing from the inventive concept, it is not intended to limit the invention otherwise than as required by the appended claims.

What is claimed is:

1. A device for testing stool samples for occult blood, said device comprising:
    (a) a stool receptor sheet, said receptor sheet being impregnated with guaiac;
    (b) a performance/control monitor on said device, said monitor including a dry button of a water-soluble hematin material positioned so as to be operable, when wetted with a developer reagent, to react with the guaiac in said receptor sheet to indicate the activity level of the guaiac and the developer reagent; and
    (c) means preventing said hematin material from reacting with the guaiac in said receptor sheet prior to being wetted with the developer reagent.

2. The device of claim 1 further comprising an impermeable pliant basal sheet on which said receptor sheet is mounted.

3. The device of claim 2 wherein said basal sheet is sufficiently larger than said receptor sheet to form an impermeable skirt surrounding said receptor sheet operable to protect a receptor sheet on another of the devices stacked below the basal sheet from air and moisture.

4. The device of claim 2 wherein said monitor includes a paper base member mounted on said receptor sheet, and said button is mounted on the surface of said base member distal of said receptor sheet wherein said base member forms said means preventing said hematin material from reacting with the guaiac.

5. A device for testing stool samples for occult blood, said device comprising:
    (a) a stool receptor sheet, said receptor sheet being impregnated with guaiac;
    (b) a dry button of a water-soluble hematin material operable, when wetted with a developer reagent, to react with the guaiac in said receptor sheet to provide an indication of the activity level of the guaiac and the developer reagent; and
    (c) a base member sandwiched between said button and said receptor sheet and secured to each, said base member preventing said hematin material from reacting with the guaiac in said receptor sheet prior to being wetted with the developer reagent.

6. The device of claim 5 wherein said base member is made of paper.

7. A device for testing stool samples for occult blood, said device comprising:
    (a) an air impermeable pliant basal sheet;
    (b) a stool receptor sheet mounted on said basal sheet and at least partly spaced therefrom, said stool receptor sheet being impregnated with guaiac; and
    (c) a dry button of a water-soluble hematin material disposed in said space between said basal sheet and said receptor sheet and secured to said basal sheet in dry form prior to mounting said receptor sheet on said basal sheet and in a manner such that said hematin material is not in chemically reactive contact with the guaiac in said receptor sheet until a developer reagent wets both the receptor sheet and the dry button, said material being operable, when wetted with the developer reagent, to react with the guaiac in said receptor sheet to provide an indication of the activity level of the guaiac and the developer reagent.

* * * * *

UNITED STATES PATENT AND TRADEMARK OFFICE
CERTIFICATE OF CORRECTION

PATENT NO.   : 4,804,518
DATED        : February 14, 1989
INVENTOR(S)  : Robert A. Levine and Stephen C. Wardlaw It is certified that error appears in the above-identified patent and that said Letters Patent is hereby corrected as shown below:

Abstract of the Disclosure, Line 4:

After "so" insert --as--

Abstract of the Disclosure, Line 11:

"reactively" should be --reactivity--

Column 1, Line 50:

"absorbant" should be --absorbent--

Column 2, Line 65:

"Fig." should be --Figs.--

Column 3, Line 59:

"quaiac" should be --guaiac--

Column 4, Line 13:

"quaiac" should be --guaiac--

UNITED STATES PATENT AND TRADEMARK OFFICE
CERTIFICATE OF CORRECTION

PATENT NO. : 4,804,518

DATED : February 14, 1989

INVENTOR(S) : Robert A. Levine and Stephen C. Wardlaw

It is certified that error appears in the above-identified patent and that said Letters Patent is hereby corrected as shown below:

Column 4, Line 17:

"heme-quaiac" should be --heme-guaiac--

Signed and Sealed this

Twelfth Day of December, 1989

Attest:

JEFFREY M. SAMUELS

Attesting Officer    Acting Commissioner of Patents and Trademarks